(12) United States Patent
Bunce et al.

(10) Patent No.: US 8,147,408 B2
(45) Date of Patent: Apr. 3, 2012

(54) MEDICAL DEVICE GUIDE LOCATOR

(75) Inventors: Steven M. Bunce, Sedro Woolley, WA (US); Blake W. Little, Bothell, WA (US)

(73) Assignee: Sonosite, Inc., Bothell, WA (US)

( * ) Notice: Subject to any disclaimer, the term of this patent is extended or adjusted under 35 U.S.C. 154(b) by 1951 days.

(21) Appl. No.: 11/216,735

(22) Filed: Aug. 31, 2005

(65) Prior Publication Data

US 2007/0049822 A1    Mar. 1, 2007

(51) Int. Cl.
*A61B 8/00* (2006.01)
(52) U.S. Cl. .......................... 600/437; 600/407
(58) Field of Classification Search ............... 600/407, 600/437, 462
See application file for complete search history.

(56) References Cited

U.S. PATENT DOCUMENTS

| | | | |
|---|---|---|---|
| 5,003,965 A | 4/1991 | Talish et al. | |
| 5,928,219 A | 7/1999 | Friend et al. | |
| 6,618,206 B2 | 9/2003 | Tarakci et al. | |
| 6,663,567 B2 | 12/2003 | Ji et al. | |
| 6,685,645 B1 | 2/2004 | McLaughlin et al. | |
| 6,733,455 B2 | 5/2004 | Mo et al. | |
| 6,773,399 B2 | 8/2004 | Xi et al. | |
| 6,866,631 B2 | 3/2005 | McLaughlin et al. | |
| 6,866,632 B1 | 3/2005 | Chou et al. | |
| 6,896,658 B2 | 5/2005 | Ji et al. | |
| 6,936,008 B2 | 8/2005 | Tarakci et al. | |
| 6,980,419 B2 | 12/2005 | Smith et al. | |
| 2003/0004414 A1 | 1/2003 | McLaughlin et al. | |
| 2004/0235142 A1 | 11/2004 | Schein et al. | |
| 2005/0131294 A1 | 6/2005 | Ji et al. | |
| 2006/0025677 A1 * | 2/2006 | Verard et al. .................. | 600/423 |

FOREIGN PATENT DOCUMENTS

| | | |
|---|---|---|
| DE | 2003/10224234 | 1/2003 |
| EP | 1 552 792 | 7/2005 |
| WO | WO 00/76575 | 12/2000 |

OTHER PUBLICATIONS

International Search Report & Written Opinion issued for PCT/US2006/032705 dated Mar. 26, 2007.

* cited by examiner

*Primary Examiner* — Brian Casler
*Assistant Examiner* — Nasir Shahrestani
(74) *Attorney, Agent, or Firm* — Fenwick & West LLP

(57) ABSTRACT

Systems and methods are shown which provide feedback with respect to the desired or proper placement of a medical device guide without introducing protuberances or other perturbations to the surface of devices used in medical procedures. Embodiments provide a biopsy needle guide bracket for use with an ultrasound transducer assembly, wherein the biopsy needle guide bracket and ultrasound transducer assembly are adapted to detect when the biopsy needle guide bracket is properly located on the ultrasound transducer assembly using one or more sensors. Embodiments may implement various sensor technology, such as Hall effect sensors, optical sensors, capacitive coupled sensors, inductive coupled sensors, and/or the like to provide feedback with respect to placement of a medical device guide.

26 Claims, 4 Drawing Sheets

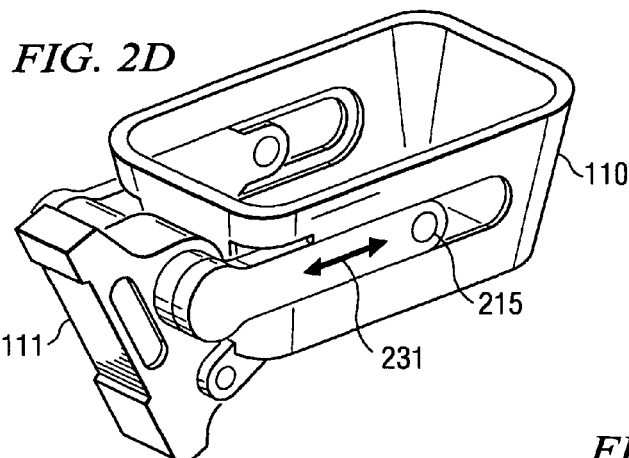
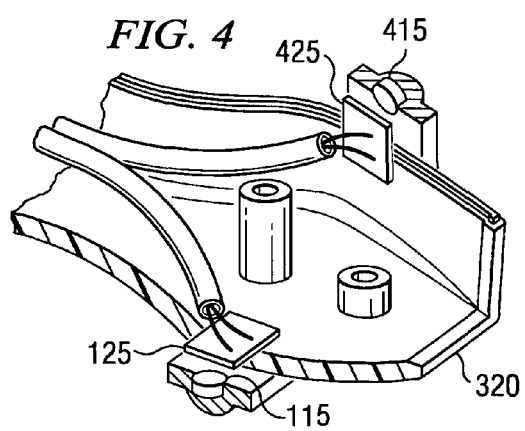
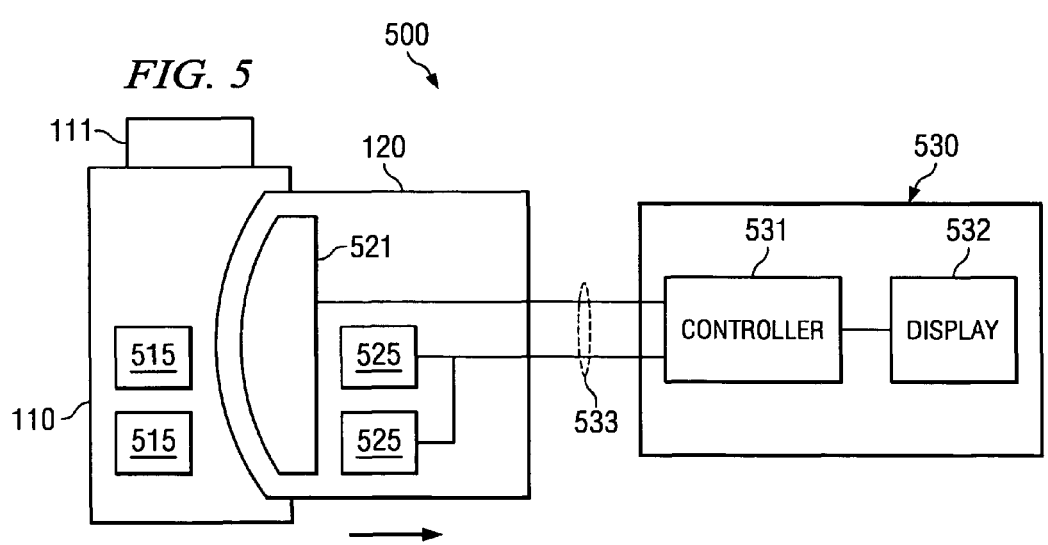

us 8,147,408 B2

MEDICAL DEVICE GUIDE LOCATOR

TECHNICAL FIELD

The invention relates generally to positioning of medical devices and more particularly to systems and methods for determining if a medical device guide is properly and/or improperly located.

BACKGROUND OF THE INVENTION

Proper movement and placement (referred to collectively as positioning) of medical devices, such as needles, catheters, drills, saws and even scalpels, is often critical in the proper performance of certain medical procedures. For example, a physician may wish to obtain a tissue sample from a small tumor or cyst in order to determine if the growth is malignant. Accordingly, a needle biopsy procedure may be performed in which the physician percutaneously extracts a tissue sample. It is critical, however, that the physician actually extract a tissue sample of the growth rather than nearby tissue. Likewise, such a growth may be found within or near other tissue structure which is subject to damage by misplaced or misguided medical devices, such a needle used in a biopsy procedure.

Accordingly, physicians often employ feedback techniques to assist them in the proper positioning of medical devices. For example, an ultrasound imaging system may be utilized to provide a visual representation of sub-dermal structure (e.g., the aforementioned growth and surrounding tissue) as well as real-time movement of a medical device (e.g., the aforementioned needle) penetrating the sub-dermal space. Accordingly, the physician often looks at a screen while trying to manually position a medical device, and thus does not look directly at the device. This is difficult at best and sometimes results in improper angles of attack and could result in improper placement of the medical device. Moreover, it is often necessary for the physician to manipulate a plurality of instruments, such as an ultrasound transducer and the needle, while looking at the screen, thereby adding to the difficulty of the procedure.

Apparatuses have been developed to assist in the proper positioning of medical devices. For example, an ultrasound transducer may be equipped with a needle guide to facilitate a needle being inserted at the proper angle of attack to reach tissue which is being imaged using an ultrasound imaging device. However, procedures benefiting from such guides often account for only a small portion (e.g., 10%) of the procedures which use such ultrasound imaging devices. Accordingly, such guides appended to an ultrasound transducer may be unneeded, and thus undesired (or perhaps even interfering), much of the time the ultrasound imaging device is used.

Some guides have therefore been adapted to be removable from the ultrasound transducer. Such removable guides have employed structure added to the surface of ultrasound transducer assemblies to facilitate their being retained on the ultrasound transducer in a proper orientation. For example, surface protuberances, such as dimples and/or pimples, may be placed on the outer surface of the ultrasound transducer and corresponding surface protuberances placed on the inner surface of a guide bracket in order to provide feedback regarding the proper positioning of the guide bracket on the ultrasound transducer assembly.

Surface protuberances on devices used in medical procedures, such as ultrasound transducers, have been found to be undesirable to the users thereof. For example, such devices are often handheld and surface protuberances present irregularities in the surface, thereby resulting in stress points experienced by the users. Where such devices are used more commonly without optional structure, such as the aforementioned guide bracket, being disposed on the device, discomfort associated with such stress points can be particularly problematic.

BRIEF SUMMARY OF THE INVENTION

The present invention provides systems and methods which provide feedback with respect to the desired or proper and/or improper placement of a medical device guide without introducing protuberances or other perturbations to the surface of devices used in medical procedures. Embodiments of the present invention provide a medical device guide and corresponding device used in medical procedures adapted to detect when the medical device guide is properly located with respect to the device used in medical procedures. For example, embodiments of the invention provide a biopsy needle guide bracket for use with an ultrasound transducer assembly, wherein the biopsy needle guide bracket and ultrasound transducer assembly are adapted to detect when the biopsy needle guide bracket is properly located on the ultrasound transducer assembly using one or more sensors.

A preferred embodiment of the invention utilizes a Hall effect sensor or sensors placed within a housing of a device used in medical procedures and a magnet or magnets correspondingly placed within the structure of a medical device guide bracket. The medical device guide bracket is preferably shaped to substantially correspond to a shape of a relevant portion of the device used in medical procedures, and thus provide a shape which generally guides the positioning of the bracket on the device, which holds the bracket in place when properly positioned on the device, and/or which is minimally obtrusive with respect to an operator of the device. However, the Hall effect sensor and corresponding magnet are preferably disposed to be juxtaposed when the bracket engages the device in the desired orientation and has engaged the device to the proper extent.

Embodiments of the present invention may implement sensor technology in addition to or in the alternative to Hall effect sensing. For example, optical sensors, capacitive coupled sensors, inductive coupled sensors, radio frequency identification (RFID) sensors, and/or the like may be utilized according to embodiments of the present invention.

According to embodiments, sensors implemented according to the present invention may be utilized to provide feedback to a user, such as to provide audible and/or visual feedback when the medical device guide bracket is properly located on the corresponding device used in medical procedures. Likewise, sensors implemented according to the present invention may be utilized to provide feedback to a user when the medical device guide bracket is improperly located on the corresponding device. Additionally or alternatively, sensors implemented according to the present invention may be utilized to control operation of one or more devices. For example, feedback from a sensor implemented according to an embodiment of the present invention may be utilized by software of a host device to suspend further operation or prevent particular operations until a medical device guide bracket is detected to be properly located. Sensors implemented according to the present invention may be utilized to indicate improper control or mode selection with respect to one or more devices. For example, feedback from a sensor implemented according to an embodiment of the present invention may be utilized to detect that an incorrect medical device guide bracket (e.g., a medical device guide bracket configured for an incorrect needle depth) has been interfaced with a medical device for which a mode of operation is selected for use of a different medical device guide bracket.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIGS. 2A-2D show a device used in medical procedures and a plurality of configurations of corresponding medical device guide brackets adapted according to an embodiment of the present invention;

FIG. 4 shows detail with respect to a housing of a device used in medical procedures according to an alternative embodiment of the invention; and FIG. 5 shows a high level block diagram of ultrasound imaging system adapted according to an embodiment of the present invention.

DETAILED DESCRIPTION OF THE INVENTION

Figure 1A:
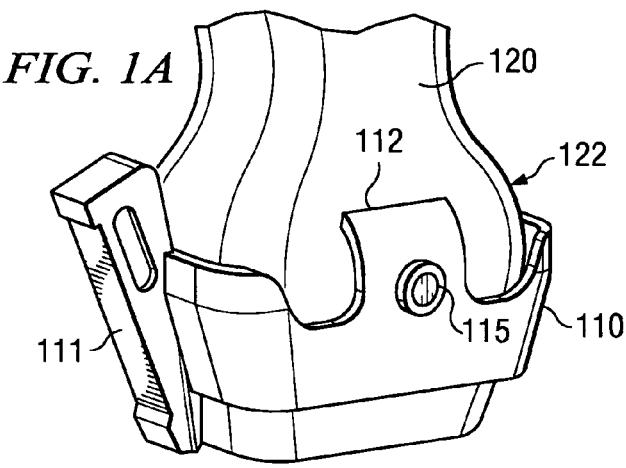
FIGS. 1A-1C show a device used in medical procedures and a corresponding medical device guide bracket adapted according to an embodiment of the present invention.
Figure 1B:
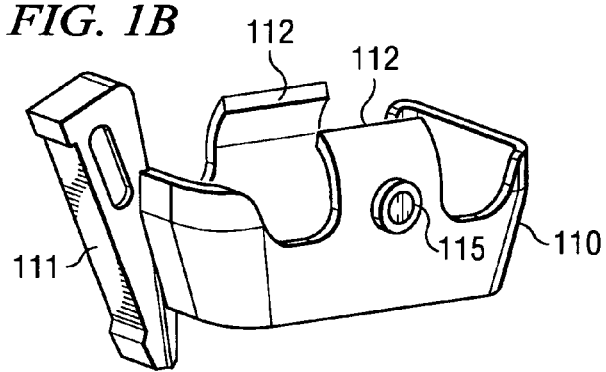
Figure 1C:
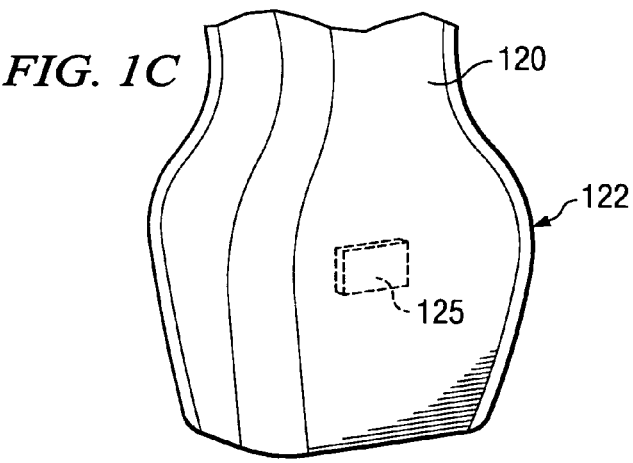

FIGS. 1A-1C show a device used in medical procedures and a corresponding medical device guide bracket adapted according to an embodiment of the present invention. Specifically, FIGS. 1A-1C illustrate an embodiment wherein medical device guide bracket 110, shown here as a biopsy needle guide bracket, and assembly 120, shown here as an ultrasound transducer assembly 120, are adapted to provide feedback with respect to the desired or proper placement of medical device guide 111 disposed on medical device guide bracket 110 without introducing protuberances or other structure to the surface of assembly 120.

It should be appreciated that, although the illustrated embodiment shows a biopsy needle guide and ultrasound transducer, embodiments of the present invention may be utilized with respect to any number of medical devices. For example, embodiments of the present invention may be utilized with respect to needles, catheters, drills, saws, scalpels, stints, and/or the like. Likewise, embodiments of the invention may be utilized with respect to numerous devices used in performing medical procedures, such as laproscopic instruments, probes, catheters, and/or the like.

FIG. 1A shows medical device guide bracket 110 installed upon assembly 120. Medical device guide bracket 110 of the illustrated embodiment is shaped to substantially correspond to a shape of a relevant portion of assembly 120. Accordingly, medical device guide bracket 110 presents a form factor which is minimally obtrusive with respect to an operator using assembly 120. Moreover, medical device guide bracket 110 includes spring clip portions 112 (more readily visible in FIG. 1B) which cooperate with corresponding structure of assembly 120 (e.g., shoulder portion 122 which is more readily visible in FIG. 1C) to hold medical device guide bracket 110 in place when properly positioned on assembly 120.

The shape of medical device guide bracket 110 may be utilized to generally guide the positioning of medical device guide bracket onto assembly 120. For example, the shape of medical device guide bracket 110 and the shape of assembly 120 prevent medical device guide bracket 110 from being placed on assembly 120 in certain undesired orientations. However, the shape of medical device guide bracket 110 and the shape of assembly 120 alone do not prevent improper positioning of medical device guide bracket 110 upon assembly 120 of the illustrated embodiment. For example, medical device guide bracket 110 may be rotated 180° with respect to assembly 120 such that the front of medical device guide bracket 110 is facing the rear. Additionally or alternatively, medical device guide bracket 110 may not be fully engaged with assembly 120, although provided in a proper orientation. For example, medical device guide bracket 110 may be partially slid onto assembly 120 without fully engaging assembly 120.

Medical device guide bracket 110 being improperly positioned on assembly 120 may result in medical device guide 111 not providing desired guidance with respect to a medical device. For example, assembly 120 may be used to provide ultrasonic imaging of a cyst, for which a biopsy is to be performed, and surrounding tissue. The assembly 120 may be adjusted to provide the subject cyst, as shown in an image presented by an ultrasound imaging device, in a position corresponding to the track of a needle inserted through medical device guide 111, when medical device guide 111 is positioned properly with respect to assembly 120. However, if medical device guide bracket 110 is improperly installed on assembly 120, medical device guide 111 may not be positioned properly with respect to assembly 120. Accordingly, a physician relying upon medical device guide 111 to guide a biopsy needle to a target cyst may instead be guided to a different area, perhaps causing serious injury to a patient.

Accordingly, medical device guide bracket 110 and assembly 120 of the illustrated embodiment are adapted to provide feedback with respect to the desired or proper placement of medical device guide bracket 110, and thus medical device guide 111, upon assembly 120. Moreover, as can be seen in FIG. 1C, feedback with respect to proper placement of medical device guide bracket 110 is provided according to the illustrated embodiment without introducing protuberances or other structure to the surface of assembly 120.

A preferred embodiment of the invention utilizes Hall effect sensor 125 placed within a housing of assembly 120 and magnet 115 correspondingly placed within the structure of medical device guide bracket 110 to provide feedback with respect to the proper placement of medical device guide bracket 110 upon assembly 120. In operation, when magnet 115 is placed in proximity to Hall effect sensor 125, the conducting properties of Hall effect sensor 125 are altered. A control system coupled to Hall effect sensor 125 may analyze signals received from Hall effect sensor 125 to determine that a magnet, presumably magnet 115, is placed in juxtaposition therewith and thus medical device guide bracket 110 is properly positioned. Accordingly, Hall effect sensor 125 and corresponding magnet 115 are preferably disposed to be juxtaposed when medical device guide bracket 110 engages assembly 120 in the desired orientation and has engaged assembly 120 to the proper extent.

Although the embodiment illustrated in FIGS. 1A and 1B provide an exterior surface of medical device guide bracket 110 conforming to a shape of magnet 115, embodiments of the invention may present exterior surfaces of medical device guide bracket 110 which do not present surface features associated with implementation of a sensor. For example, magnet 115 of embodiments of the present invention may be disposed with a wall of medical device guide bracket 110 without a protrusion in an exterior surface of medical device guide bracket 110 where magnet 115 is sufficiently thin and/or the wall of medical device guide bracket 110 is sufficiently thick. Such an embodiment may be advantageous where it is desired to eliminate a potential point of stress or other discomfort experienced by a user holding assembly 120 having medical device guide bracket 110 attached thereto. However, it is expected that the amount of use of medical device guide bracket 110 will be relatively small as compared to the amount of use of assembly 120 without medical device guide bracket 110 installed thereon. Accordingly, embodiments of the present invention eliminate surface perturbations used with respect to properly positioning medical device guide bracket 110 irrespective of whether medical device guide bracket 110 itself has surface perturbations thereon.

Magnet 115 of embodiments of the invention is selected to provide a size and magnetic field which results in signals being provided by Hall effect sensor 125 indicative of when medical device guide bracket 110 is placed in a desired position. For example, the size of magnet 115 may be selected so as to cause Hall effect sensor 125 to provide signals indicative of when medical device guide bracket 110 is placed in a desired position only when magnet 115 is positioned within a very small area. Additionally or alternatively, the magnet 115 may be oriented in medical device guide bracket 110 such that the magnetic field provided thereby is polarized or otherwise orientated to cause Hall effect sensor 125 to provide signals indicative of when medical device guide bracket 110 is placed in a desired position only when magnet 115 is positioned within a very small area.

Magnet 115 and/or Hall effect sensor 125 of embodiments of the invention may additionally or alternatively be adapted to provide information in addition to when medical device guide bracket 110 is placed in a desired position. For example, magnet 115 and Hall effect sensor 125 may cooperate to provide a first signal when magnet 115 is within proximity to Hall effect sensor 125, such as may be used by a controller coupled to Hall effect sensor 125 to determine that medical device guide bracket 110 is near to its proper position. Magnet 115 and Hall effect sensor 125 of the foregoing example preferably provide a second signal when magnet 115 is in juxtaposition with sensor 125, such as may be used by the controller to determine that medical device guide bracket 110 is in its proper position. The foregoing first and second signals may be provided as a result of Hall effect sensor 125 providing different variations in conducting as a function of the strength of the field experienced from magnet 115, the relative positions of one or more poles of magnet 115 with respect to Hall effect sensor 125, etcetera.

Information in addition to when medical device guide bracket 110 is placed in a desired position provided by magnet 115 and/or Hall effect sensor 125 of embodiments of the invention may include information with respect to a configuration of medical device guide bracket 110. For example, Hall effect sensor 125 may comprise a plurality of sensing positions, such as sensing positions 221-223 shown in FIG. 2A. Different configurations of medical device guide bracket 110 may be provided with a magnet disposed in a position corresponding to different ones of sensing positions 221-223. For example, medical device guide bracket 110 of FIG. 2B, having medical device guide 111 configured for relatively deep needle penetration, has magnet 211 disposed at a first position corresponding to sensing position 221. However, medical device guide bracket 110 of FIG. 2B, having medical device guide 111 configured for relatively shallow needle penetration, has magnet 213 disposed at a third position corresponding to sensing position 223. It should be appreciated that a third medical device guide bracket (not shown) may have a different configuration, such as medical device guide 111 configured for needle penetration to a depth between that of the aforementioned relatively deep needle penetration and relatively shallow needle penetration.

The various different configurations detected according to embodiments of the invention need not be fixed, but rather may be adjustable, if desired. Directing attention to FIG. 2D, an embodiment wherein medical device guide 111 is pivotally coupled to medical device guide bracket 110 for selectable adjustment of medical device guide 111 is shown. As medical device guide 111 of the illustrated embodiment is adjusted, such as to select a particular depth of needle penetration, arm 231 slides, thereby changing the position of magnet 215. Sensor 215, using sensing positions 221-223 or perhaps continuous sensing along the length of sensor 215, detects the position of magnet 215 and thus the configuration of medical device guide 111.

Accordingly, not only may an embodiment of the present invention detect that each of the foregoing medical device guide brackets are properly positioned upon assembly 120, but such an embodiment may further determine the configuration of the medical device guide bracket by analyzing the particular Hall effect sensor or sensors detecting the proximity of a magnet. A determination with respect to the configuration of the medical device guide bracket may be utilized in providing information with respect to the operation of a system to a user thereof. For example, embodiments of the present invention may provide a warning to a user that an improper operational mode has been selected for use with the presently detected medical device guide bracket configuration. Additionally or alternatively, embodiments of the invention may operate to provide information with respect to the presently detected medical device guide bracket configuration, such as an operational mode (e.g., software setting) which should be used with the medical device guide bracket configuration, a depth of needle penetration associated with the medical device guide bracket configuration, or other information associated with or relevant to the medical device guide bracket configuration, its use, etcetera.

It should be appreciated that detection of different configurations according to embodiments of the present invention is not limited to any particular number of configurations or to the particular configurations shown. For example, using sensing positions 221-223 illustrated in FIG. 2A, an embodiment of the invention may make determinations with respect to the proper positioning of 7 different configurations of medical device guide bracket configurations (e.g., 1 using a magnet at sensing position 221, 1 using a magnet at sensing position 222, 1 using a magnet at sensing position 223, 1 using a magnet at sensing positions 221 and 222, 1 using a magnet at sensing positions 221 and 223, 1 using a magnet at sensing positions 222 and 223, and 1 using a magnet at sensing positions 221, 222, and 223).

Figure 3A:
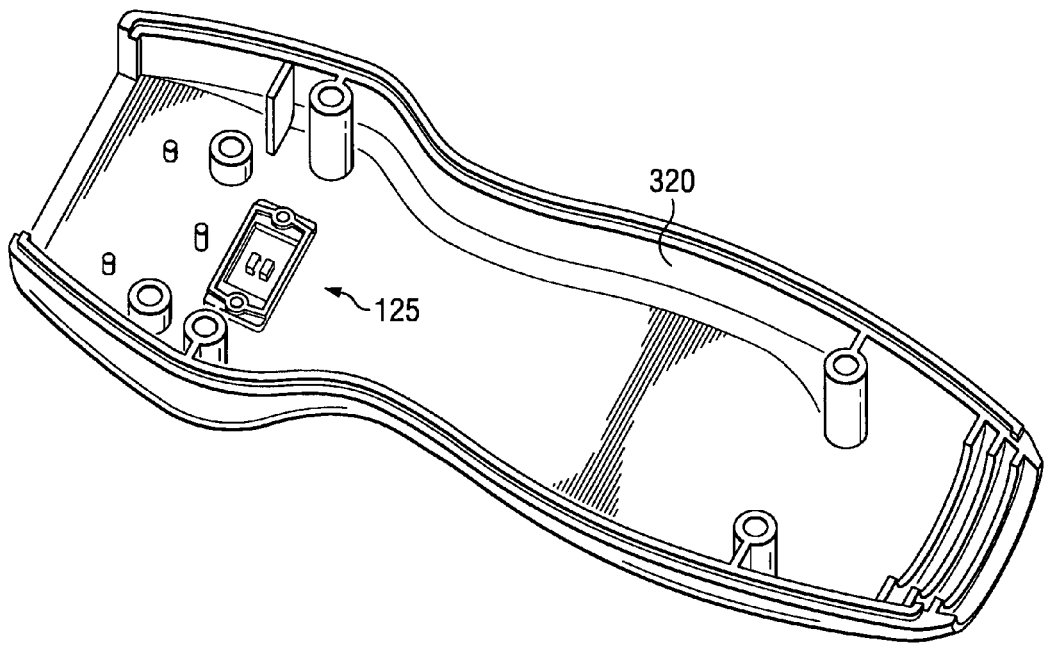
FIGS. 3A and 3B show detail, according to one embodiment, with respect to a housing of the device used in medical procedures of FIG. 1.
Figure 3B:
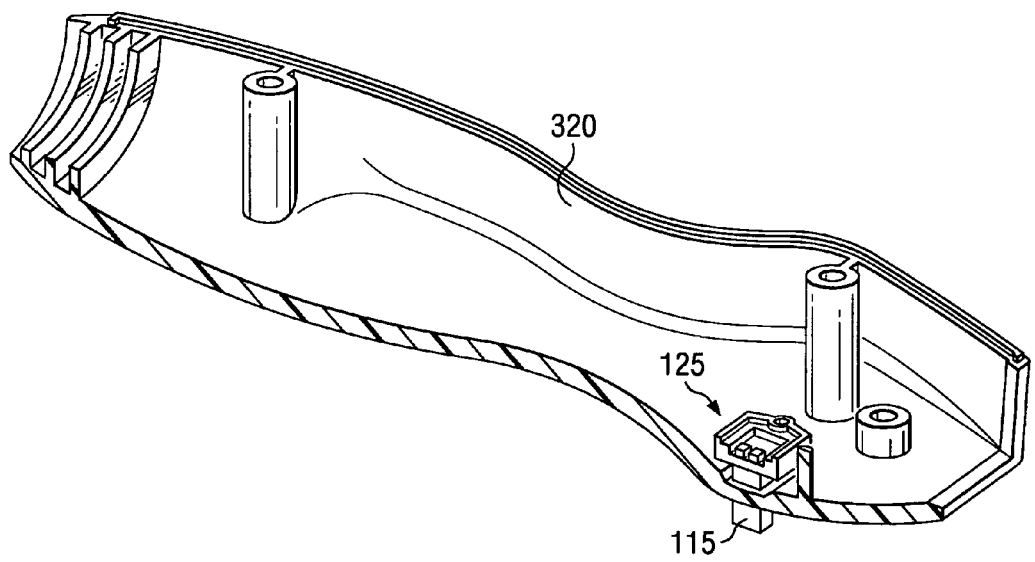

Directing attention to FIGS. 3A and 3B, it can be seen that Hall effect sensor 125 of the illustrated embodiment is placed along a centerline of housing 320 of assembly 120. Hall effect sensor 125 of embodiments of the invention is disposed as shown in FIG. 3A to provide a configuration which is readily implemented with respect to a two-piece housing assembly and which does not interfere with other components, such as a transducer array, signal cables, etcetera. It should be appreciated, however, that embodiments of the present invention may implement various placements of sensors in addition to or in the alternative to that shown.

Figure 2A:
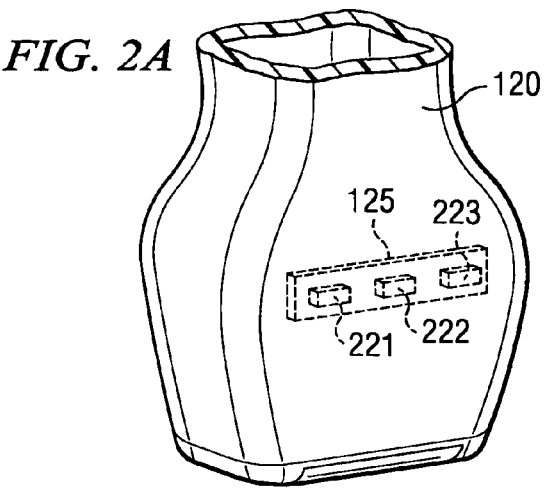
Figure 2B:
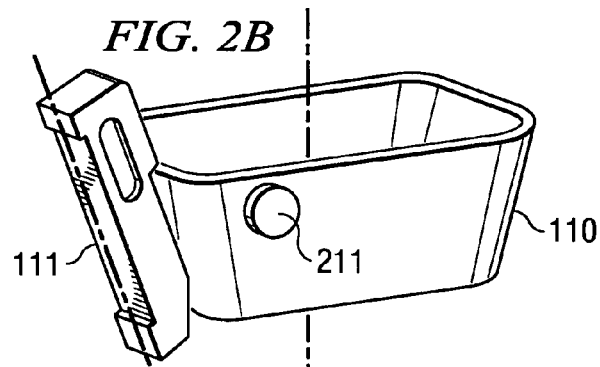
Figure 2C:
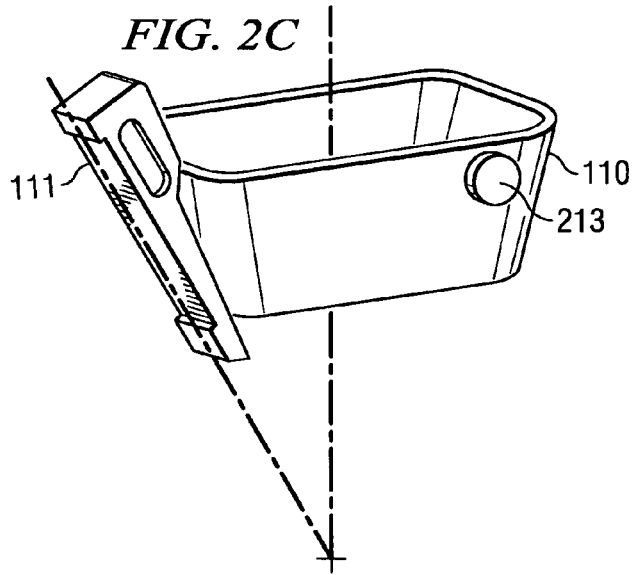

Embodiments of the present invention may utilize a plurality of sensors. For example, second Hall effect sensor 425 may be disposed at a 90° angle with respect to Hall effect sensor 125, as shown in FIG. 4. Of course, there is no limitation to the sensors being disposed in the particular configuration of FIG. 4. For example, such an additional sensor may be disposed in a second housing of assembly 120 substantially as illustrated in FIG. 2A. Such an additional sensor may be utilized in providing additional information to a user. For example, a second sensor may be used to detect when medical device guide bracket 110 is disposed in a particular incorrect position and thus a controller coupled thereto may provide appropriate information, such as instructions as to how to correct the installation of medical device guide bracket 110. In one such an implementation according to an embodiment of the present invention, a single magnet 115 is provided while 2 Hall effect sensors 125 are provided. Thus when a particular one of the Hall effect sensors 125 experiences a magnet field, an orientation of medical device guide bracket 110 may be determined.

The use of a plurality of sensors may additionally or alternatively be used according to embodiments of the invention to provide a high level of confidence with respect to the positioning of medical device guide bracket 110. For example, the embodiment of FIG. 4 includes Hall effect sensor 125 disposed within a front surface of assembly 120 provided in combination with Hall effect sensor 425 disposed within a side surface of assembly 120 and medical device guide bracket 110 is provided with magnets 115 and 415 disposed to correspond to these Hall effect sensors when medical device guide bracket 110 is properly positioned on assembly 120. A controller coupled to the Hall effect sensors may not determine that medical device guide bracket 110 is properly positioned until an appropriate signal is received from each such Hall effect sensor. Accordingly, an anomalous signal from one such Hall effect sensor, such as may result from a malfunctioning sensor or being exposed to a stray magnetic field, will be unlikely to result in an incorrect determination that medical device guide bracket 110 is properly positioned.

Although the illustrated embodiment has been described with reference to a Hall effect sensor and corresponding magnet, embodiments of the present invention may implement various sensor technologies, such as optical sensors, capacitive coupled sensors, inductive coupled sensors, RFID sensors, and/or the like, in the alternative to or in combination with the aforementioned Hall effect sensors. For example, embodiments of the present invention may dispose a light pipe (e.g., fiber optic line) such that an end thereof is flush with an external surface of assembly 120 (e.g., at a position corresponding to a position of an edge of medical device guide bracket 110 when installed on assembly 120) and another end thereof in communication with an optic sensor (e.g., a photo diode). When medical device guide bracket 110 is positioned properly upon assembly 120, the exposed end of the light pipe will be covered and thus the optic sensor provides a signal to a controller coupled thereto according to an embodiment of the invention. It should be appreciated that normal handling of assembly 120 may result in covering the exposed end of such a light pipe (e.g., by surfaces of a hand). Accordingly, an optical sensor embodiment of the present invention utilizes a plurality of light pipes, preferably disposed at different locations on assembly 120, in order to provide a high level of confidence with respect to determining when medical device guide bracket 110 is disposed in a proper position. For example, an embodiment may detect that one or more optical sensors are obscured by medical device guide bracket 110 and that one or more optical sensors are not obscured by medical device guide bracket 110 (e.g., such as by a hole or transparent part of medical device guide bracket 110 being provided in juxtaposition with a particular light pipe at the surface of assembly 120).

According to another embodiment, a light source is provided within the assembly housing (such as at a position corresponding to Hall effect sensor 125 of FIG. 4) with a light window allowing the light to pass through the assembly housing. The medical device guide bracket may comprise a light pipe embedded therein and having a plurality of light interfaces facing the assembly (such as at positions corresponding to magnets 115 and 415 of FIG. 4). The assembly housing may further include a light window allowing light to pass through an optical sensor disposed therein (such as at a position corresponding to Hall effect sensor 425 of FIG. 4). Accordingly, when positioned correctly, light will pass from the light source, through the light pipe, to the optical sensor. The optical sensor may be designed to react to specific light frequency in order to avoid false determinations that a medical device guide bracket has been installed due to detecting ambient light.

An embodiment of the invention utilizing RFID technology may comprise an RFID tag within the medical device guide bracket which is powered and read when in proximity to a RFID sensor disposed within the assembly. When in close proximity to the RFID sensor, the RFID tag may be powered and data read therefrom. Information provided by the RFID tag may indicate the medical device guide bracket configuration and/or other information.

Directing attention to FIG. 5, a high level block diagram of ultrasound imaging system 500. Ultrasound imaging system 500 of the illustrated embodiment includes ultrasound imaging device 530 (such as may comprise the TITAN™, the 180PLUS™, the ELITE™, or the ILOOK™ ultrasound imaging devices available from SonoSite, Inc., Bothell, Wash. U.S.A.) coupled to assembly 120 via cable 533. Ultrasound imaging device 530 of the illustrated embodiment includes controller 531, such as may comprise a microcontroller, memory, and an instruction set providing operation as described herein, and display 532, such as may comprise a liquid crystal display (LCD) or other screen for displaying graphical images and/or text. Assembly 120 of the illustrated embodiment includes transducer array 521 and sensors 525. It should be appreciated that, although separate signal paths are shown in cable 533 with respect to transducer array 521 and sensors 525, signals of one or more transducer and/or sensor may share a common signal path, such as through multiplexing, signal combining, etcetera.

Sensors 525 may implement any desired sensor technology, such as Hall effect, optical, capacitive, inductive, and/or the like. Medical device guide bracket 111 (shown only partially engaging assembly 120) illustrated in FIG. 5 includes corresponding sensor members 515, such as may comprise a magnet, an opaque surface, a transparent surface, a plate, a coil, and/or the like, which cooperate with sensors 525 to provide feedback with respect to the desired or proper placement of medical device guide bracket 110, and thus medical device guide 111.

In operation, a user may select an operational mode of ultrasound imaging device 530 with which medical device guide 111 should be used. For example, a user may select a biopsy mode in which a particular image feature, corresponding to a tissue growth of interest, is targeted in an image displayed on display 532 (e.g., the tissue growth is focused upon and placed at a particular position in the displayed image). Controller 531 may analyze signals from sensors 525 and make a determination with respect to whether medical device guide bracket 110 is properly positioned with respect to assembly 120. As mentioned above, such a determination may include analyzing signals associated with one or more of sensors 525 to provide information with respect to how a user may correct the placement of medical device guide bracket 110, such as by providing instructions and/or graphics on display 532. If it is determined that medical device guide bracket 110 is not properly positioned, controller 531 may prevent operation of ultrasound imaging device 530 in the selected mode. If it is determined that medial device guide bracket 110 is properly positioned, controller 531 may allow operation of ultrasound imaging device 530 in the desired mode. For example, display 532 may provide a real-time image of the target tissue and surrounding tissue, showing the progression of a needle guided by medical device guide 111 toward the target tissue. Because medical device guide bracket 110 is properly positioned with respect to assembly 120, and thus medical device guide 111 is properly positioned for the imaging mode selected, a physician using ultrasound imaging system 500 to perform a biopsy procedure may be confident that the needle will obtain a sample of the target tissue.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A system comprising:
    an imaging device used in medical procedures, said imaging device having an ultrasound transducer assembly;
    a first sensor disposed in said ultrasound transducer assembly of said imaging device;
    a guide assembly having a bracket and a medical device guide attached to said bracket, said bracket being shaped to hold at least a portion of said ultrasound transducer assembly of said imaging device with said first sensor thererein; and
    a sensor member carried by said bracket, said sensor member being in a predetermined position with respect to said medical device guide, wherein said first sensor is configured to indicate target alignment between said ultrasound transducer assembly and said medical device guide when said sensor member is juxtaposed with said first sensor.

2. The system of claim 1, wherein said first sensor is disposed in said device used in medical procedures without resulting in perturbation of an external surface of said device used in medical procedures.

3. The system of claim 1, wherein said first sensor comprises a Hall effect sensor and said sensor member comprises a magnet.

4. The system of claim 1, wherein said first sensor comprises an optical sensor and said sensor member comprises an opaque portion of a bracket attached to said medical device guide.

5. The system of claim 1, wherein said first sensor comprises an optical sensor and said sensor member comprises a transparent portion of a bracket attached to said medical device guide.

6. The system of claim 1, wherein said first sensor comprises an optical sensor and said sensor member comprises a light pipe disposed in a bracket attached to said medical device guide.

7. The system of claim 1, wherein said device used in medical procedures comprises said ultrasound transducer assembly.

8. The system of claim 1, further comprising:
    a controller, said controller operable to determine if said medical device guide is disposed in a proper position using signals from said first sensor responsive to said sensor member.

9. The system of claim 8, wherein said controller is further operable to prevent at least one operation of a host system if it is determined that said medical device guide is not disposed in said proper position.

10. The system of claim 8, wherein said controller is further operable to monitor said first sensor to determine if said medical device guide is disposed in said proper position when a predetermined mode of operation of said host system is selected.

11. The system of claim 8, wherein said controller is further operable to monitor said first sensor to determine a configuration of said medical device guide.

12. The system of claim 1, further comprising:
    a second sensor disposed in said device used in medical procedures.

13. The system of claim 12, further comprising:
    a controller, said controller operable to determine if said medical device guide is disposed in a proper position using signals from both said first sensor and said second sensor.

14. The system of claim 12, further comprising:
    a controller, said controller operable to provide information with respect to disposing said medical device guide in a proper position using signals both said first sensor and said second sensor.

15. A method performed by a control system of a medical device comprising:
    receiving by the control system information from a first sensor that is disposed within an ultrasound transducer assembly of a device used in medical procedures and that engages with a bracket having a sensor member disposed therein, wherein the bracket is adapted to juxtapose, said sensor member with said first sensor; and determining with the control system if said bracket is in a desired relative position with respect to said ultrasound transducer assembly of said device used in medical procedures using information from said first sensor as affected by said sensor member.

16. The method of claim 15, further comprising:

determining a configuration of said bracket using information from said first sensor as affected by said sensor member.

17. The method of claim 15, further comprising:

determining if said bracket is in proximity to said desired position using information from said first sensor as affected by said sensor member.

18. The method of claim 15, wherein said ultrasound transducer assembly of the device includes a second sensor and said determining if said bracket is in said desired position comprises:

determining if a particular one of said first and second sensors is in juxtaposition with said sensor member.

19. The method of claim 15, wherein said bracket includes another sensor member disposed therein and determining if said bracket is in said desired position comprises:

determining if said first sensor is in juxtaposition with said sensor member; and determining if said second sensor is in juxtaposition with said another sensor member disposed in said bracket.

20. The method of claim 18, further comprising:

providing information with respect to correcting a position of said bracket as a function of information provided from said first and second sensors.

21. The method of claim 15, wherein said first sensor is disposed within said device without providing alteration to an external surface of said device in an area corresponding to said first sensor.

22. A system comprising:

a needle guide;

an ultrasound transducer assembly having a sensor disposed therein; and a bracket adapted to engage said ultrasound transducer assembly, said needle guide being attached to said bracket and to hold said needle guide in a target alignment with respect to said ultrasound transducer assembly, said bracket having a sensor member, wherein said first sensor is configured to indicate said target alignment between said ultrasound transducer assembly and said needle guide when said sensor member is juxtaposed with said first sensor.

23. The system of claim 22, wherein the sensor comprises a Hall effect sensor and said sensor member comprises a magnet.

24. The system of claim 22, further comprising:

a controller coupled to said sensor, said controller operable to analyze a signal from said sensor to determine if said bracket is disposed in said predetermined relative position.

25. The system of claim 22, wherein said ultrasound transducer assembly includes a housing, wherein said sensor is disposed internal to said housing.

26. The system of claim 25, wherein an external surface of said housing is unaffected by said sensor disposed therein.

* * * * *

UNITED STATES PATENT AND TRADEMARK OFFICE
CERTIFICATE OF CORRECTION

| | | |
|---|---|---|
| PATENT NO. | : 8,147,408 B2 | Page 1 of 1 |
| APPLICATION NO. | : 11/216735 | |
| DATED | : April 3, 2012 | |
| INVENTOR(S) | : Steven M. Bunce et al. | |

It is certified that error appears in the above-identified patent and that said Letters Patent is hereby corrected as shown below:

Column 10, line 61, Claim 14, please add --from-- before "both".

Signed and Sealed this
Fifth Day of June, 2012

David J. Kappos
*Director of the United States Patent and Trademark Office*